United States Patent
Park (10) Patent No.: US 9,125,618 B2
(45) Date of Patent: Sep. 8, 2015

(54) PROVIDING AN ELASTIC IMAGE IN AN ULTRASOUND SYSTEM

(75) Inventor: Sang Shik Park, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 424 days.

(21) Appl. No.: 13/156,519

(22) Filed: Jun. 9, 2011

(65) Prior Publication Data

US 2011/0306883 A1     Dec. 15, 2011

(30) Foreign Application Priority Data

Jun. 9, 2010 (KR) .................. 10-2010-0054143

(51) Int. Cl.
| | |
|---|---|
| *A61B 8/00* | (2006.01) |
| *A61B 8/08* | (2006.01) |
| *A61B 5/00* | (2006.01) |
| *G01S 7/52* | (2006.01) |

(52) U.S. Cl.
CPC .............. *A61B 8/485* (2013.01); *A61B 5/0048* (2013.01); *A61B 8/0833* (2013.01); *G01S 7/52042* (2013.01)

(58) Field of Classification Search
CPC ..... A61B 8/485; A61B 5/0048; A61B 8/5223
USPC ......................................... 600/407, 437–472
See application file for complete search history.

(56) References Cited

U.S. PATENT DOCUMENTS

| | | | |
|---|---|---|---|
| 7,443,381 | B2 | 10/2008 | Mo |
| 8,386,927 | B1 | 2/2013 | Franklin et al. |

(Continued)

FOREIGN PATENT DOCUMENTS

| | | |
|---|---|---|
| EP | 1 665 987 A1 | 6/2006 |
| EP | 1 815 796 A1 | 8/2007 |

(Continued)

OTHER PUBLICATIONS

European Search Report issued in European Patent Application No. EP 11168935.2 dated Oct. 5, 2011.

(Continued)

*Primary Examiner* — Mark Remaly
(74) *Attorney, Agent, or Firm* — McDermott Will & Emery LLP (57) ABSTRACT

Embodiments for providing an elastic image are disclosed. In one embodiment, an ultrasound system comprises: an ultrasound data acquisition unit configured to transmit and receive ultrasound signals to and from a living body to output ultrasound data corresponding to a plurality of frames while applying compression to the living body; and a processing unit configured to extract frames from a $(n-1)^{th}$ frame to a $(n-i)^{th}$ frame on a basis of a $n^{th}$ frame, wherein n indicates an integer larger than one and i indicates a positive integer, detect an optimal frame for forming an elastic image among the extracted frames by using first displacement between the $n^{th}$ frame and each of the extracted frames based on the ultrasound data, calculate second displacement between the optimal frame and the $n^{th}$ frame based on the ultrasound data, and form the elastic image based on the second displacement.

11 Claims, 8 Drawing Sheets

(56) References Cited

U.S. PATENT DOCUMENTS

| | | | |
|---|---|---|---|
| 2006/0084870 A1* | 4/2006 | Kim et al. | 600/437 |
| 2008/0232660 A1 | 9/2008 | Hyun et al. | |
| 2009/0182234 A1* | 7/2009 | Perrey et al. | 600/443 |
| 2009/0270730 A1* | 10/2009 | Azuma et al. | 600/443 |
| 2009/0292205 A1 | 11/2009 | Osaka | |
| 2010/0016722 A1 | 1/2010 | Shin et al. | |
| 2010/0125199 A1 | 5/2010 | Joo et al. | |
| 2010/0125205 A1 | 5/2010 | Park et al. | |
| 2010/0268084 A1 | 10/2010 | Osaka et al. | |

FOREIGN PATENT DOCUMENTS

| | | |
|---|---|---|
| JP | 2010-022828 | 2/2010 |
| JP | 2010-119630 A | 6/2010 |
| KR | 10-2008-0086683 A | 9/2008 |
| KR | 10-2010-0055743 A | 5/2010 |
| KR | 10-2010-0056713 A | 5/2010 |
| WO | 2008/010500 A1 | 1/2008 |
| WO | WO 2009/001007 A2 | 12/2008 |
| WO | 2009060732 A1 | 5/2009 |

OTHER PUBLICATIONS

Korean Notice of Allowance dated Jun. 26, 2013 issued in Korean Application No. 10-2010-0054143.
Japanese Non-Final Office Rejection mailed in corresponding Japanese Application No. 2011-129304 on Jan. 13, 2015; 9 pages with English translation.

* cited by examiner

PROVIDING AN ELASTIC IMAGE IN AN ULTRASOUND SYSTEM

CROSS-REFERENCE TO RELATED APPLICATIONS

The present application claims priority from Korean Patent Application No. 10-2010-0054143 filed on Jun. 9, 2010, the entire subject matter of which is incorporated herein by reference.

TECHNICAL FIELD

The present disclosure generally relates to ultrasound systems, and more particularly to providing an elastic image in an ultrasound system.

BACKGROUND

Recently, an ultrasound system has been extensively used in the medical field due to its non-invasive and non-destructive nature. Modern high-performance ultrasound imaging systems and techniques are commonly used to produce two and three-dimensional ultrasound images of internal features of patients.

Generally, the ultrasound image is displayed in a Brightness mode (B-mode) by using reflectivity caused by an acoustic impedance difference between the tissues of a target object. However, if the reflectivity of the target object is hardly different from those of the neighboring tissues such as tumor, cancer or the like, then it is not easy to recognize the target object in the B-mode image. Further, an ultrasound elastic imaging technology has been developed to display an image of the target object by using mechanical characteristics of the target object. Such technology is very helpful for diagnosing lesions such as cancers. The tumor or cancer is relatively stiffer than the neighboring tissues. Thus, when pressure is uniformly applied, a variation of the tumor or cancer is typically smaller than those of the neighboring tissues.

The elasticity of a tissue is measured by using ultrasound data obtained before and after applying the pressure to the tissue. A compression plate mounted on an ultrasound probe may be used to apply the pressure to the tissue. A user may press the compression plate on the target object, thereby applying the pressure to the tissues of the target object. In such a case, strain data in the tissues may vary according to the pressure applied by the user. Thus, the video quality of an elastic image may be changed according to the pressure applied to the tissue.

SUMMARY

Embodiments for forming an elastic image in an ultrasound system are disclosed herein. In one embodiment, by way of non-limiting example, an ultrasound system comprises: an ultrasound data acquisition unit configured to transmit and receive ultrasound signals to and from a living body to output ultrasound data corresponding to a plurality of frames while applying compression to the living body; and a processing unit in communication with the ultrasound data acquisition unit, the processing unit being configured to extract frames from a $(n-1)^{th}$ frame to a $(n-i)^{th}$ frame on a basis of a $n^{th}$ frame, wherein n indicates an integer larger than one and i indicates a positive integer, detect an optimal frame for forming an elastic image among the extracted frames by using first displacement between the $n^{th}$ frame and each of the extracted frames based on the ultrasound data, calculate second displacement between the optimal frame and the $n^{th}$ frame based on the ultrasound data, and form the elastic image based on the second displacement.

In another embodiment, there is provided a method of providing an elastic image, comprising: a) transmitting and receiving ultrasound signals to and from a living body to output ultrasound data corresponding to a plurality of frames while applying compression to the living body; b) extracting frames from a $(n-1)^{th}$ frame to a $(n-i)^{th}$ frame on a basis of a $n^{th}$ frame, wherein n indicates an integer larger than one and i indicates a positive integer; c) detecting an optimal frame for forming an elastic image among the extracted frames by using first displacement between the $n^{th}$ frame and each of the extracted frames based on the ultrasound data; d) calculating second displacement between the optimal frame and the $n^{th}$ frame based on the ultrasound data; and e) forming the elastic image based on the second displacement.

In yet another embodiment, there is provided a computer readable medium comprising computer executable instructions configured to perform the following acts: a) acquiring ultrasound data corresponding to a plurality of frames while applying compression to the living body; b) extracting frames from a $(n-1)^{th}$ frame to a $(n-i)^{th}$ frame on a basis of a $n^{th}$ frame, wherein n indicates an integer larger than one and i indicates a positive integer; c) detecting an optimal frame for forming an elastic image among the extracted frames by using first displacement between the $n^{th}$ frame and each of the extracted frames based on the ultrasound data; d) calculating second displacement between the optimal frame and the $n^{th}$ frame based on the ultrasound data; and e) forming the elastic image based on the second displacement.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
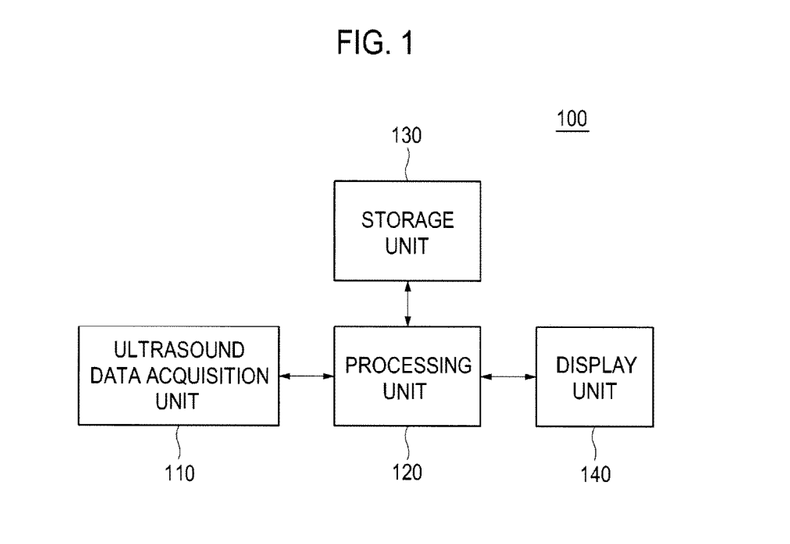
FIG. 1 is a block diagram showing an illustrative embodiment of an ultrasound system.

Referring to FIG. 1, an ultrasound system 100 in accordance with an illustrative embodiment is shown. As depicted therein, the ultrasound system 100 may include an ultrasound data acquisition unit 110. The ultrasound data acquisition unit 110 may be configured to transmit and receive ultrasound signals to and from a living body while applying compression to the target object, and output ultrasound data. The living body may include a plurality of target objects (e.g., blood vessels, a heart, a lesion etc.).

Figure 2:
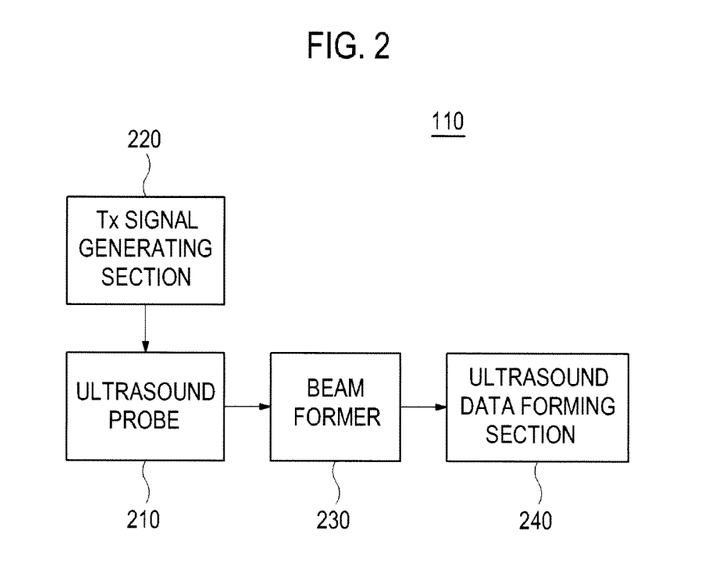
FIG. 2 is a block diagram showing an illustrative embodiment of an ultrasound data acquisition unit.

FIG. 2 is a block diagram showing an illustrative embodiment of the ultrasound data acquisition unit 110. Referring to FIG. 2, the ultrasound data acquisition unit 110 may include an ultrasound probe 210, a transmit (Tx) signal generating section 220, a beam former 230 and an ultrasound data forming section 240.

The ultrasound probe 210 may apply the compression provided from an external to the living body. The ultrasound probe 210 may include a plurality of elements (not shown) for reciprocally converting between ultrasound signals and electrical signals. The ultrasound probe 210 may be configured to transmit ultrasound signals to the living body. The ultrasound probe 210 may be further configured to receive ultrasound signals (i.e., ultrasound echo signals) from the living body and output electrical signals ("received signals"). The received signals may be analog signals. The ultrasound probe 210 may include a convex probe, a linear probe and the like.

Figure 3:
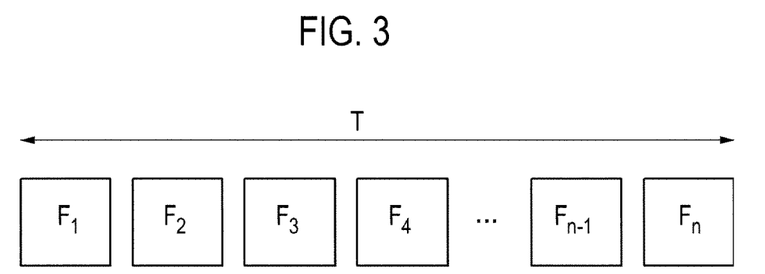
FIG. 3 is a schematic diagram showing an example of frames.

The Tx signal generating section 220 may be configured to control the transmission of the ultrasound signals. The Tx signal generating section 220 may be further configured to generate electrical signals ("Tx signals") in consideration of the elements and focal points. In one embodiment, the Tx signal generating section 220 may generate Tx signals for obtaining a plurality of frames $F_i(1 \leq i \leq N)$ while applying compression to the living body, as shown in FIG. 3. Thus, the ultrasound probe 210 may convert the Tx signals provided from the Tx signal generating section 220 into the ultrasound signals, transmit the ultrasound signals to the living body and receive the ultrasound echo signals from the living body to thereby output the received signals. The frame may include a brightness mode image. However, it should be noted herein that the frame may not be limited thereto.

The beam former 230 may be configured to convert the received signals provided from the ultrasound probe 210 into digital signals. The beam former 230 may be further configured to apply delays to the digital signals in consideration of the elements and the focal points to output digital receive-focused signals.

The ultrasound data forming section 240 may be configured to form ultrasound data based on the digital receive-focused signals provided from the beam former 230. The ultrasound data may include radio frequency data. However, it should be noted herein that the ultrasound data may not be limited thereto. The ultrasound data forming section 240 may be further configured to perform various signal processing (e.g., gain adjustment) upon the digital receive-focused signals. In one embodiment, the ultrasound data forming section 240 may form the ultrasound data corresponding to each of the frames $F_i(1 \leq i \leq N)$ based on the digital receive-focused signals provided from the beam former 230.

Referring back to FIG. 1, the ultrasound system 100 may further include a processing unit 120 in communication with the ultrasound data acquisition unit 110. The processing unit 120 may include a central processing unit, a microprocessor or a graphic processing unit. However, it should be noted herein that the processing unit 120 may not be limited thereto.

Figure 4:
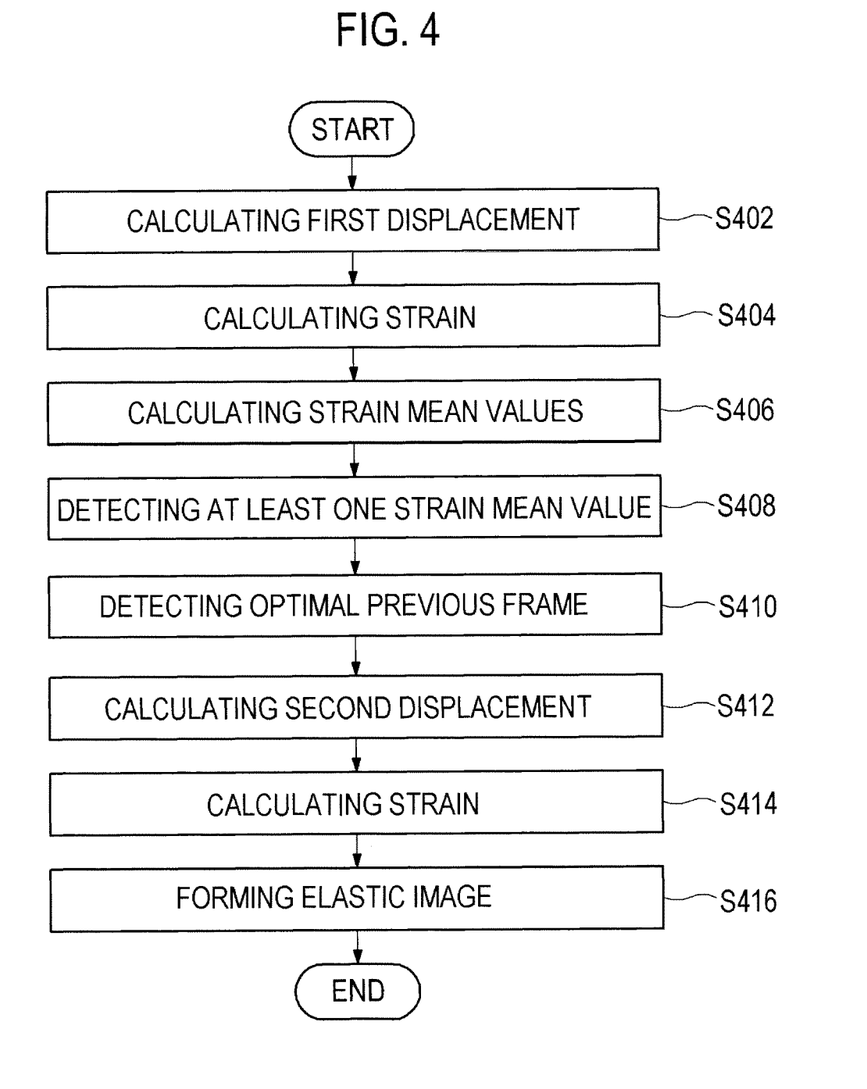
FIG. 4 is a flow chart showing a process of forming an elastic image in accordance with a first embodiment.

FIG. 4 is a flow chart showing a process of forming an elastic image in accordance with a first embodiment. The processing unit 120 may be configured to calculate displacement ("first displacement") based on the ultrasound data corresponding to a current frame and the ultrasound data corresponding to a predetermined number of previous frames, at step S402 in FIG. 4. The first displacement may be roughly calculated.

Figure 5:
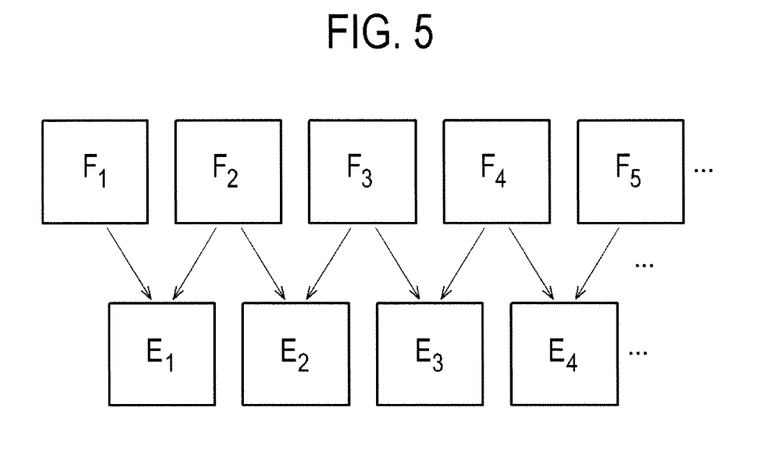
FIG. 5 is a schematic diagram showing an example of calculating displacement.

Generally, the displacement $D_{i-1}$, wherein i is a positive integer, corresponding to an elastic image $E_{i-1}$ between a current frame $F_i$ and a previous frame $F_{i-1}$ was calculated based on the ultrasound data provided from the ultrasound data acquisition unit 110, as shown in FIG. 5.

In the embodiment, the processing unit 120 may be configured to extract the predetermined number of the previous frames based on the current frame. The processing unit 120 may be further configured to calculate the first displacement corresponding to the elastic images between the current frame and each of the previous frames based on the ultrasound data.

Figure 6:
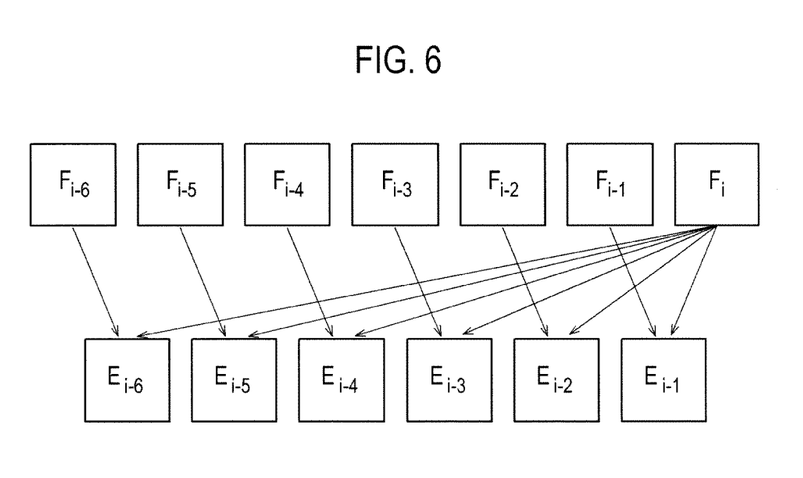
FIG. 6 is a schematic diagram showing an example of calculating the displacement in accordance with the embodiment.

As one example, the processing unit 120 may be configured to extract the predetermined number of the previous frames $F_{i-1}$ to $F_{i-6}$ based on the current frame $F_i$, as shown in FIG. 6. The processing unit 120 may be further configured to calculate the first displacement $D_{i-1}$ to $D_{i-6}$ corresponding to the elastic images to $E_{i-1}$ to $E_{i-6}$ between the current frame $F_i$ and each of the previous frames $F_{i-1}$ to $F_{i-6}$ based on the ultrasound data, as shown in FIG. 6.

As another example, the processing unit 120 may be configured to extract the predetermined number of the previous frames $F_{i-1}$ to $F_{i-6}$ based on the current frame $F_i$. The processing unit 120 may be further configured to set a region of interest ("ROI") on the current frame $F_i$ and the extracted previous frames $F_{i-1}$ to $F_{i-6}$. The processing unit 120 may be further configured to calculate the first displacements between the ROI of the current frame $F_i$ and the ROI of each of the extracted previous frames $F_{i-1}$ to $F_{i-6}$.

As yet another example, the processing unit 120 may be configured to extract the predetermined number of the previous frames $F_{i-1}$ to $F_{i-6}$ based on the current frame $F_i$. The processing unit 120 may be further configured to calculate axial motions corresponding to the elastic images $E_{i-1}$ to $E_{i-6}$ between the current frame $F_i$ and each of the previous frames $F_{i-1}$ to $F_{i-6}$. The methods of calculating the axial motion (e.g., blocking matching) are well known in the art. Thus, they have not been described in detail so as not to unnecessarily obscure the present invention. The processing unit 120 may be further configured to calculate the first displacement $D_{i-1}$ to $D_{i-6}$ corresponding to the elastic images $E_{i-1}$ to $E_{i-6}$ based on the calculated axial motions.

As yet another example, the processing unit 120 may be configured to extract the predetermined number of the previous frames $F_{i-1}$ to $F_{i-6}$ based on the current frame $F_i$. The processing unit 120 may be further configured to set the ROI on the current frame $F_i$ and the previous frames $F_{i-1}$ to $F_{i-6}$. The processing unit 120 may be also configured to calculate the axial motions corresponding to the elastic images $E_{i-1}$ to $E_{i-6}$ between the current frame $F_i$ and each of the previous frames $F_{i-1}$ to $F_{i-6}$. The processing unit 120 may be further configured to calculate the first displacement $D_{i-1}$ to $D_{i-6}$ corresponding to the elastic images $E_{i-1}$ to $E_{i-6}$ based on the calculated axial motions.

The processing unit 120 may be configured to calculate strain corresponding to each of the elastic images based on the first displacement, at step S404 in FIG. 4. The methods of calculating the strain are well known in the art. For example, the processing unit 120 may calculate a differential value of the first displacement as the strain.

The processing unit 120 may be configured to calculate a strain mean value corresponding to each of the elastic images based on the calculated strain, at step S406 in FIG. 4.

Figure 7:
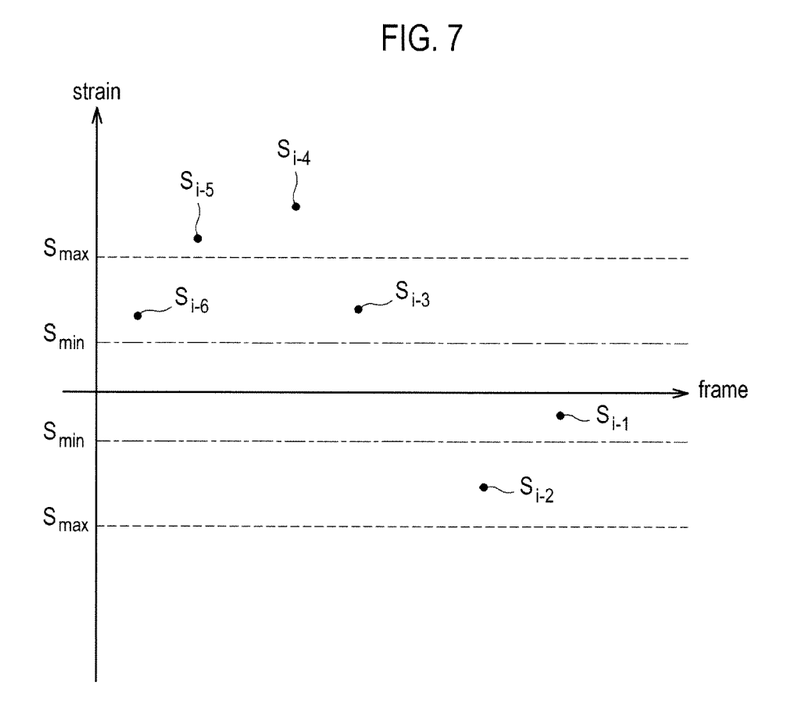
FIG. 7 is a schematic diagram showing an example of a strain threshold range.

The processing unit 120 may be configured to compare the calculated strain mean values with a predetermined strain threshold range to detect at least one strain mean value corresponding to the strain threshold range, at step S408 in FIG. 4. For example, the processing unit 120 may compare each of the strain mean values $S_{i-1}$ to $S_{i-6}$ with the strain threshold range $S_{min}$ to $S_{max}$ to detect strain mean values $S_{i-2}$, $S_{i-3}$ and $S_{i-6}$, which are comprised in the strain threshold range $S_{min}$ to $S_{max}$, as shown in FIG. 7.

The processing unit 120 may be configured to detect an optimal previous frame for forming an optimal elastic image from at least one previous frame corresponding to the at least one strain mean value, at step S410 in FIG. 4. For example, the processing unit 120 may calculate standard deviation of the strain for the previous frames $F_{i-2}$, $F_{i-3}$ and $F_{i-6}$ corresponding to the detected strain mean values $S_{i-2}$, $S_{i-3}$ and $S_{i-6}$. The processing unit 120 may further extract a previous frame (e.g., $F_{i-3}$) corresponding to minimum standard deviation as the optimal.

Although it is described above that the processing unit 120 may detect the previous frame corresponding to the minimum standard deviation as the optimal previous frame for forming the elastic image, the processing unit 120 may further detect the previous frame corresponding to a strain mean value, which is closest to a predetermined threshold in the strain threshold range, as the optimal previous frame. Alternatively, the processing unit 120 may detect the previous frame corresponding to a strain mean value, which is smaller than or larger than the predetermined threshold in the strain threshold range, as the optima previous frame.

The processing unit 120 may be configured to calculate displacement ("second displacement") between the optimal previous frame and the current frame based on the ultrasound data provided from the ultrasound data acquisition unit 110, at step S412 in FIG. 4. For example, the processing unit 120 may calculate the second displacement between the optimal previous frame $F_{i-3}$ and the current frame $F_i$ based on the ultrasound data provided from the ultrasound data acquisition unit 110.

The processing unit 120 may be configured to calculate the strain based on the second displacement, at step S414 in FIG. 4. The processing unit 120 may be configured to form the optimal elastic image based on the strain, at step S416 in FIG. 4. The methods of forming the elastic image based on the strain are well known in the art. Thus, they have not been described in detail so as not to unnecessarily obscure the present invention.

Figure 8:
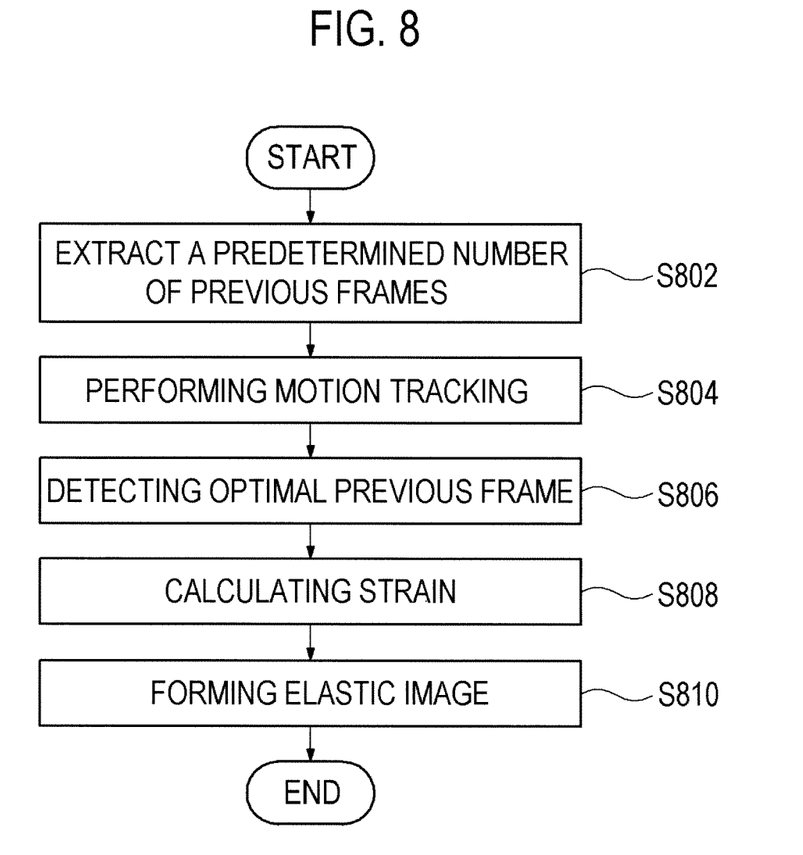
FIG. 8 is a flow chart showing a process of forming the elastic image in accordance with the second embodiment.

FIG. 8 is a flow chart showing a process of forming an elastic image in accordance with a second embodiment. The processing unit 120 may be configured to extract a predetermined number of previous frames based on a current frame, at step S802 in FIG. 8.

The processing unit 120 may be configured to perform motion tracking (e.g., block matching) between the current frame and each of the extracted previous frames to detect lateral motion between the current first frame and each of the previous first frames, at step S804 in FIG. 8.

The processing unit 120 may be configured to detect an optimal previous frame for forming an optimal elastic image from the extracted previous frames, at step S806 in FIG. 8. For example, the processing unit 120 may compare the detected lateral motion to detect a previous frame corresponding to minimum lateral motion. The processing unit 120 may further set the detected previous frame as the optimal previous frame.

Although it is described above that the processing unit 120 may detect the lateral motion between the current frame and the previous frame, the processing unit 120 may further detect elevation motion between a current three-dimensional frame and a previous three-dimensional frame. The three-dimensional frame may include a three-dimensional image. However, it should be noted herein that the three-dimensional frame may not be limited thereto.

The processing unit 120 may be configured to calculate strain between the current frame and the optimal previous frame based on the ultrasound data provided from the ultrasound data acquisition unit 110, at step S808 in FIG. 8.

The processing unit 120 may be configured to form the optimal elastic image based on the calculated strain, at step S810 in FIG. 8.

Figure 9:
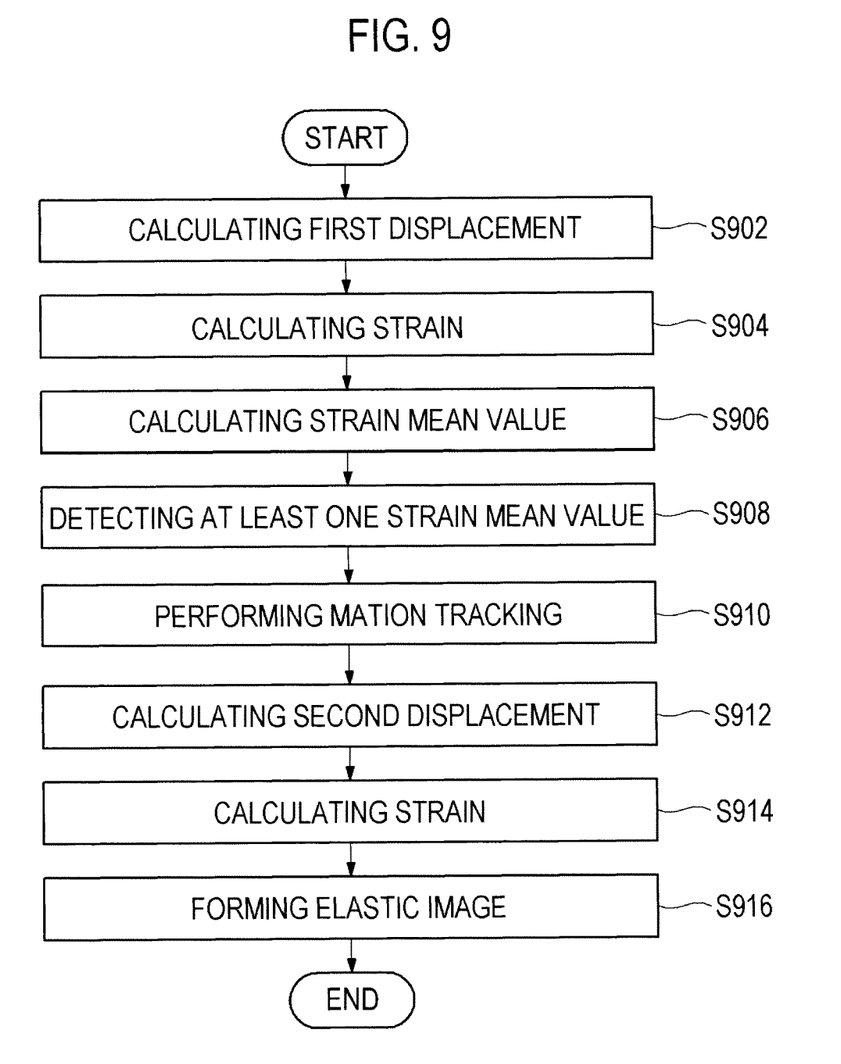
FIG. 9 is a flow chart showing a process of forming an elastic image in accordance with a third embodiment.

FIG. 9 is a flow chart showing a process of forming an elastic image in accordance with a third embodiment. The processing unit 120 may be configured to calculate the first displacement based on the ultrasound data corresponding to the current frame and the ultrasound data corresponding to the predetermined number of previous frames, at step S902 in FIG. 9. The step S902 in FIG. 9 may be similar to the step S402 in FIG. 4. Thus, it has not been described in detail.

The processing unit 120 may be configured to calculate the strain corresponding to each of the elastic images based on the first displacement, at step S904 in FIG. 9.

The processing unit 120 may be configured to calculate the strain mean value corresponding to each of the elastic images based on the calculated strain, at step S906 in FIG. 9. The step S906 in FIG. 9 may be similar to the step S406 in FIG. 4. Thus, it has not been described in detail.

The processing unit 120 may be configured to compare the calculated strain mean values with the strain threshold range to detect at least one strain mean value corresponding to the strain threshold range, at step S908 in FIG. 9.

The processing unit 120 may be configured to perform the motion tracking (e.g., block matching) between the current frame and at least one previous frame corresponding to the at least one strain mean value to detect the lateral motion between the current frame and the at least one previous frame, at step S910 in FIG. 9.

Although it is described above that the processing unit 120 may detect the lateral motion between the current frame and the previous frame, the processing unit 120 may further detect the elevation motion between a current three-dimensional frame and a previous three-dimensional frame. The three-dimensional frame may include a three-dimensional image. However, it should be noted herein that the three-dimensional frame may not be limited thereto.

The processing unit 120 may be configured to detect the optimal previous frame for forming an optimal elastic image, ate step S912 in FIG. 9. For example, the processing unit 120 may compare the detected lateral motion to detect a previous frame corresponding to minimum lateral motion. The processing unit 120 may further set the detected previous frame as the optimal previous frame.

The processing unit 120 may be configured to calculate second displacement between the optimal previous frame and the current frame based on the ultrasound data provided from the ultrasound data acquisition unit 110, at step S914 in FIG. 9.

The processing unit 120 may be configured to calculate the strain based on the second displacement, at step S914 in FIG.

9. The processing unit 120 may be configured to form the optimal elastic image based on the strain, at step S916 in FIG. 9.

Figure 10:
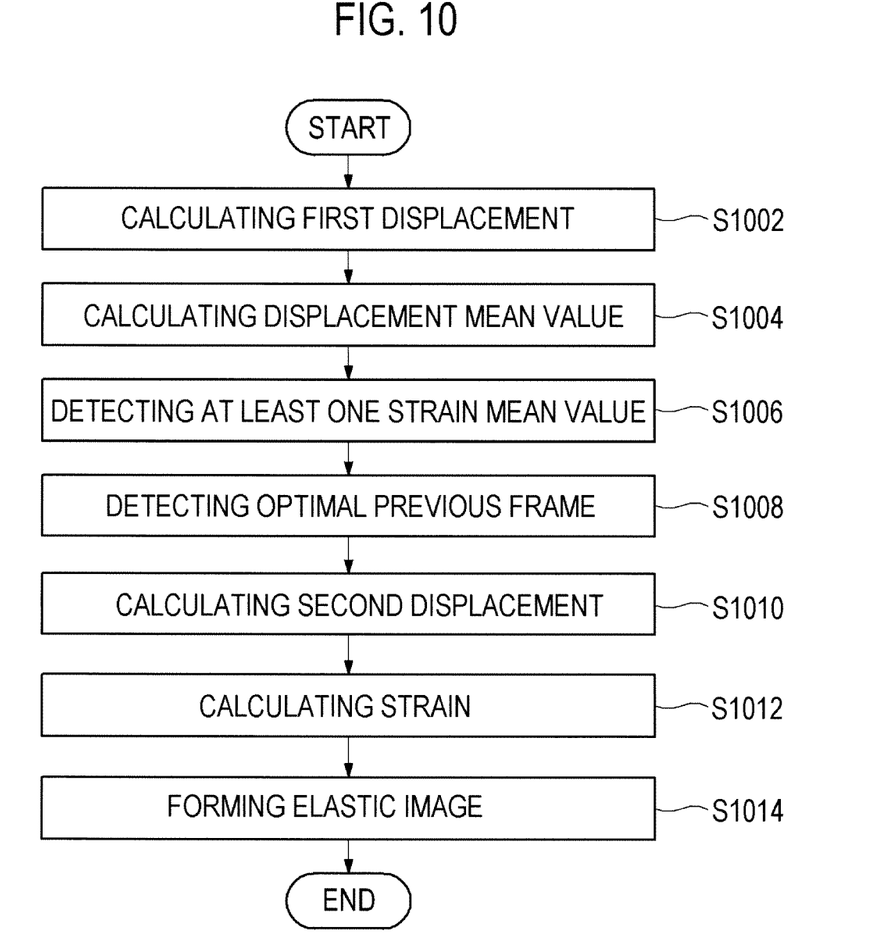
FIG. 10 is a flow chart showing a process of forming an elastic image in accordance with a fourth embodiment.

FIG. 10 is a flow chart showing a process of forming an elastic image in accordance with a fourth embodiment. The processing unit 120 may be configured to calculate the first displacement based on the ultrasound data corresponding to the current frame and the ultrasound data corresponding to the predetermined number of previous frames, at step S1002 in FIG. 10. The step S1002 in FIG. 10 may be similar to the step S402 in FIG. 4. Thus, it has not been described in detail.

The processing unit 120 may be configured to calculate a displacement mean value corresponding to each of the elastic images based on the displacement, at step S1004 in FIG. 10.

The processing unit 120 may be configured to compare the displacement mean values with a predetermined displacement threshold range to detect at least one displacement mean value corresponding to the displacement threshold range, at step S1006 in FIG. 10. The step S1006 in FIG. 10 may be similar to the step S408 in FIG. 4. Thus, it has not been described in detail.

The processing unit 120 may be configured to detect the optimal previous frame for forming an optimal elastic image, at step S1008 in FIG. 10. For example, the processing unit 120 may calculate standard deviation of the strain for at least one previous frames corresponding to the at least one displacement mean value. The processing unit 120 may further compare the calculated standard deviation to extract a previous frame corresponding to a minimum standard deviation. The processing unit 120 may further set the extracted previous frame as the optimal previous frame.

Although it is described above that the processing unit 120 may detect the previous frame corresponding to the minimum standard deviation as the optimal previous frame for forming the elastic image, the processing unit 120 may further detect the previous frame corresponding to a displacement mean value, which is closest to a predetermined threshold in the displacement threshold range, as the optimal previous frame, or detect the previous frame corresponding to a displacement mean value, which is smaller than or larger than the threshold in the displacement threshold range, as the optima previous frame.

The processing unit 120 may be configured to calculate second displacement between the optimal previous frame and the current frame based on the ultrasound data provided from the ultrasound data acquisition unit 110, at step S1010 in FIG. 10.

The processing unit 120 may be configured to calculate the strain based on the second displacement, at step S1012 in FIG. 10. The processing unit 120 may be configured to form the optimal elastic image based on the strain, at step S1014 in FIG. 10.

Referring back to FIG. 1, the ultrasound system 100 may further include a storage unit 130. The storage unit 130 may store the ultrasound data acquired by the ultrasound data acquisition unit 110. The storage unit 130 may further store the displacement and the strain calculated by the processing unit 120.

The ultrasound system 100 may further include a display unit 140. The display unit 140 may display the elastic image formed by the processing unit 120. The display unit 140 may further display the frames formed by the processing unit 120.

In another embodiment, the present invention may provide a computer readable medium comprising computer executable instructions configured to perform the following acts: a) acquiring ultrasound data corresponding to a plurality of frames while applying compression to the living body; b) extracting frames from a $(n-1)^{th}$ frame to a $(n-i)^{th}$ frame on a basis of a $n^{th}$ frame, wherein n indicates an integer larger than one and i indicates a positive integer; c) detecting an optimal frame for forming an elastic image among the extracted frames by using first displacement between the $n^{th}$ frame and each of the extracted frames based on the ultrasound data; d) calculating second displacement between the optimal frame and the $n^{th}$ frame based on the ultrasound data; and e) forming the elastic image based on the second displacement. The computer readable medium may comprise a floppy disk, a hard disk, a memory, a compact disk, a digital video disk, etc.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   an ultrasound probe configured to receive ultrasound signals for obtaining a plurality of frames while applying compression to a living body during a predetermined time;
   a beam former configured to convert the received ultrasound signals into digital signals;
   an ultrasound data forming section configured to form ultrasound data corresponding to the plurality of frames using the digital signals output from the beam former; and
   a processor in communication with the ultrasound data forming section, wherein the processor is configured to:
   extract frames from a $(n-1)^{th}$ frame to a $(n-i)^{th}$ frame which are previous frames of a current $n^{th}$ frame among the plurality of frames,
   calculate a first displacement between the $n^{th}$ frame and each of the $(n-1)^{th}$ frame to the $(n-i)^{th}$ frame of the ultrasound data,
   calculate a first strain using the first displacement between the $n^{th}$ frame and each of the $(n-1)^{th}$ frame to the $(n-i)^{th}$ frame of the ultrasound data,
   calculate strain mean values using the first strain,
   detect an optimal frame for forming an elastic image among the extracted frames based on the strain mean values,
   calculate strain based on a displacement between the optimal frame and the $n^{th}$ frame, and
   form the elastic image using the strain corresponding to the optimal frame.

2. The ultrasound system of claim 1, wherein the processor is further configured to:
   compare the strain mean values with a predetermined strain threshold range to detect at least one strain mean value corresponding to the strain threshold range;
   detect the optimal frame based on the at least one strain mean value;
   calculate second displacement between the $n^{th}$ frame and the optimal frame of the ultrasound data; and
   form the elastic image using the second displacement.

3. The ultrasound system of claim 2, wherein the processor is further configured to:

calculate a standard deviation of the first strain for at least one frame corresponding to the at least one strain mean value; and compare the standard deviation to extract a frame corresponding to a minimum standard deviation as the optimal frame.

4. The ultrasound system of claim 2, wherein the processor is further configured to:

set a region of interest on the $(n-1)^{th}$ frame to the $(n-i)^{th}$ frame and the $n^{th}$ frame; and calculate the first displacement corresponding to the region of interest.

5. The ultrasound system of claim 2, wherein the processor is further configured to:

perform motion tracking between the $n^{th}$ frame and each of the $(n-1)^{th}$ frame to the $(n-i)^{th}$ frame to calculate axial motion; and calculate the first displacement using the axial motion.

6. The ultrasound system of claim 2, wherein the processor is further configured to:

set a region of interest on the $(n-1)^{th}$ frame to the $(n-i)^{th}$ frame and the $n^{th}$ frame;

calculate axial motion corresponding to the region of interest; and calculate the first displacement using the axial motion.

7. The ultrasound system of claim 1, wherein the processor is further configured to:

perform motion tracking between the $n^{th}$ frame and each of the $(n-1)^{th}$ frame to the $(n-i)^{th}$ frame of the ultrasound data to calculate lateral motion or elevation motion; and detect the optimal frame among the $(n-1)^{th}$ frame to the $(n-i)^{th}$ frame based on the lateral motion or elevation motion.

8. The ultrasound system of claim 1, wherein the processor is further configured to:

compare the strain mean values with a predetermined strain threshold range to detect at least one strain mean value corresponding to the strain threshold range;

perform motion tracking between the $n^{th}$ frame and at least one frame corresponding to the at least one strain mean value to detect lateral motion or elevation motion;

detect the optimal frame corresponding to the at least one strain mean value using the lateral motion or the elevation motion;

calculate the second displacement between the optimal frame and the $n^{th}$ frame of the ultrasound data;

calculate second strain using the second displacement; and form the elastic image using the calculated second strain.

9. The ultrasound system of claim 1, wherein the processor is further configured to:

calculate displacement mean values using the first displacement;

compare the displacement mean values with a predetermined displacement threshold range to detect at least one displacement mean value corresponding to the displacement threshold range;

detect the optimal frame corresponding to the at least one displacement mean value corresponding to the displacement threshold range;

calculate a second displacement between the optimal frame and the $n^{th}$ frame of the ultrasound data;

calculate second strain of the second displacement; and form the elastic image of the calculated second strain.

10. The ultrasound system of claim 1, wherein the optimal frame corresponds to a minimum standard deviation of the strain.

11. The ultrasound system of claim 1, wherein the optimal frame corresponds to minimum lateral motion.

* * * * *